United States Patent [19]

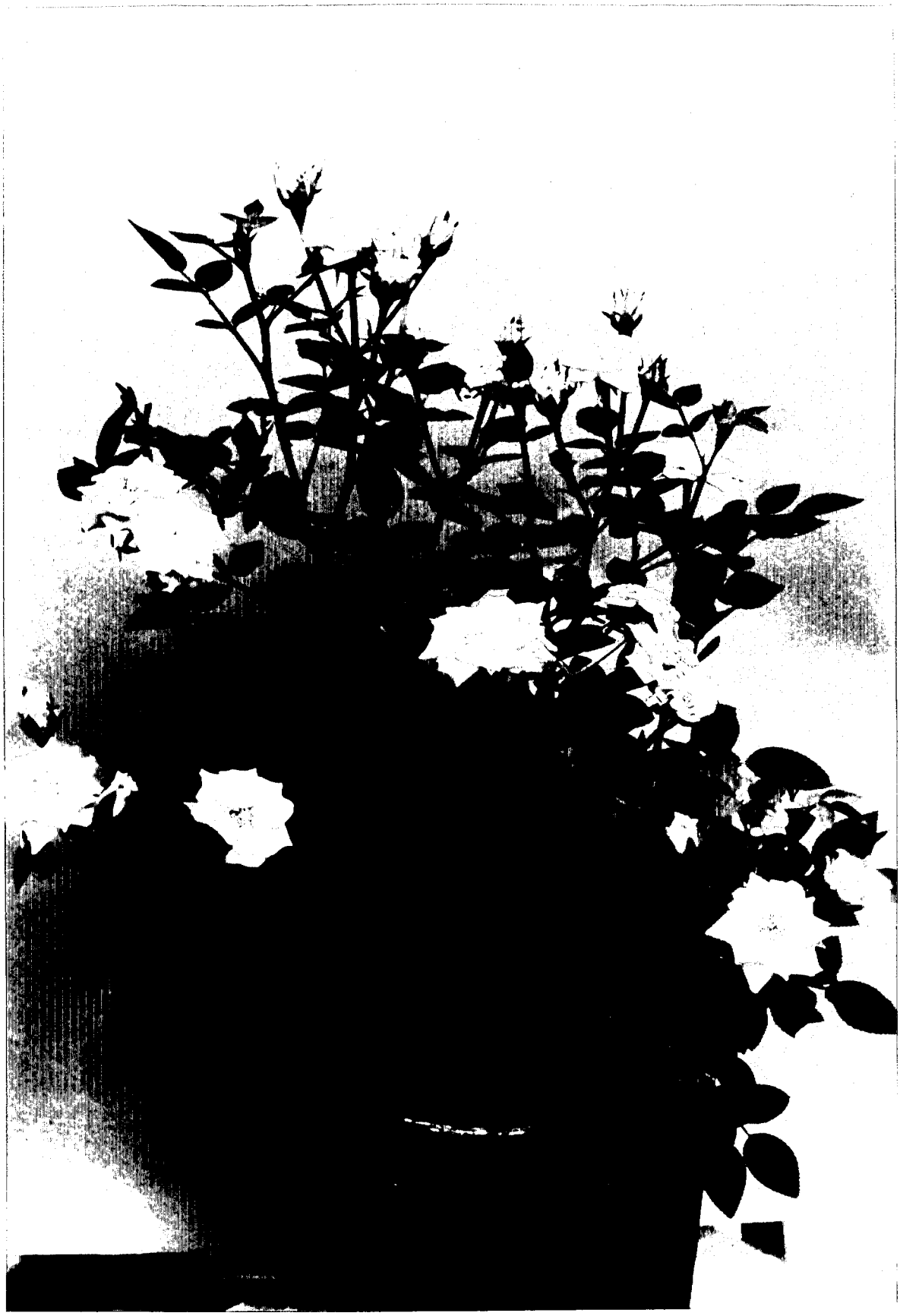

de Ruiter

[11] Patent Number: Plant 5,768

[45] Date of Patent: Jul. 22, 1986

[54] ROSE PLANT RUIPIKO

[75] Inventor: Gijsbert de Ruiter, Ab Hazerswoude, Netherlands

[73] Assignee: Jackson & Perkins Company, Medford, Oreg.

[21] Appl. No.: 667,636

[22] Filed: Nov. 2, 1984

[51] Int. Cl.[4] ..... A01H 5/00

[52] U.S. Cl. ..... Plt./9

[58] Field of Search ..... Plt./9

*Primary Examiner*—James R. Feyrer

*Attorney, Agent, or Firm*—Manford R. Haxton

[57] ABSTRACT

A miniature rose variety having dwarf, compact, free blooming plant, producing Tyrian rose blooms approximately 1" across, of heavy substance, suitable for use as a pot plant.

1 Drawing Figure

This present invention relates to a new and distinct variety of rose plant of the miniature class which was originated by crossing an unnamed variety with the variety Amruda.

The primary objective of this breeding was to produce a new rose variety of small size suitable for production of flowering pot plants as well as useful for garden decoration. This objective was substantially achieved along with other desirable improvements as evidenced by the following unique combination of characteristics which are outstanding in the new variety and which distinguish it from its parents as well as from all other varieties of which I am aware:

1. Readily propagated and grown on its own roots by cuttings;
2. Initial blooms when plants are approximately 6" tall;
3. Blooms carried in clusters as well as one per stem;
4. Bud and bloom color near Tyrian Rose (Wilson); and
5. Heavy petal substance causing flower to retain form until dehiscence.

Asexual reproduction of this new variety by cuttings, as performed at Irvine, Calif., and Hazerswoude, Holland, shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with the Wilson's Horticultural Colour Chart except where ordinary dictionary significance of color is indicated:

Parentage:
- *Seed parent.*—Unnamed variety.
- *Pollen parent.*—Amruda.

Classification:
- *Botanical.*—Rosa hybrid.
- *Commercial.*—Miniature.

FLOWER

Observations made from specimens grown in a greenhouse at Irvine, Calif. in August.

Blooming habit: Continuous.

Bud:
- *Size.*—½" when petals start to unfurl.
- *Form.*—Pointed ovoid.
- *Color.*—When sepals first divide, Tyrian Rose 24; when half blown, upper side of petals Tyrian Rose 24/1; lower side of petals Tyrian Rose 24/1.
- *Sepals.*—Color: Scheeles Green 860. Three appendaged sepals normally appendaged. Two appendaged sepals hairy edged.
- *Receptacle.*—Color: Scheeles Green 860. Shape: Funnel. Size: Relatively large. Surface: Slightly pubescent.
- *Peduncle.*—Length: Short. Surface: Glandular. Color: Light green. Strength: Stiff, erect.

Open bloom:
- *Size.*—Small. Average open size 1".
- *Borne.*—Singly, in clusters; irregular.
- *Stems.*—Short.
- *Form.*—When first open, flat. Permanence: Retains its form to the end.
- *Petalage.*—Number of petals under normal conditions: 28–30.
- *Color.*—Center of flower: Upper side of petals, Near Tyrian Rose 24/2; reverse side of petals, Near Tyrian Rose 24/2. Base of petals, Near White. Major color: Tyrian Rose 24/1 to 24/2.
- *Variegations.*—Many petals have prominent white midribs.
- *Discoloration.*—General tonality at end of fourth day: Lightens to Tyrian Rose 24/1.
- *Fragrance.*—None.

Petals:
- *Texture.*—Thick.
- *Shape.*—Nearly round.
- *Form.*—Edges slightly quilled.
- *Arrangement.*—Imbricated.
- *Persistence.*—Drop off cleanly.
- *Lastingness.*—On the plant, very long. As cut flower, very long.

Reproductive parts:
- *Anthers.*—Large, many. Color: Yellow. Arrangement: Regular around styles.
- *Filaments.*—Color: Very light green.
- *Styles.*—Color: Very light green.
- *Stigmas.*—Color: White.

PLANT

Form: Bush.

Growth: Vigorous, dwarf, upright.

Foliage: Number of leaflets on normal mid-stem leaves: 5 or 7.

*Size.*—Small.

*Quantity.*—Normal.

*Color.*—New foliage: Light green, suffused lightly with Garnet Brown 00918/3. Old foliage: Normal green.

Leaflets:

*Shape.*—Oval pointed.

*Texture.*—Leathery.

*Edge.*—Serrated.

*Serration.*—Single, small.

*Petiole.*—Rachis: Color: Green. Underside: With prickles. Upper edges, glandular.

*Stipules.*—Medium, bearded.

*Disease resistance.*—Resistant to mildew, under normal growing conditions at Irvine, Calif.

Wood:

*New wood.*—Color: Light green. Bark: Smooth.

*Old wood.*—Color: Green. Bark: Smooth.

Prickles:

*Quantity.*—On main canes from base: Few. On laterals from main canes: Few.

*Form .*—Long, straight.

*Color when young.*—Green.

Small prickles:

*Quantity.*—On main stalks, none. On laterals, None.

I claim:

1. A new and distinct variety of rose plant of the miniature class, substantially as herein shown and described, characterized particularly as to novelty by the unique combination of its dwarf, compact, free blooming plant, producing Tyrian rose blooms approximately 1″ across, of heavy substance, suitable for use as a pot plant.

* * * * *